United States Patent [19]
Cook et al.

[11] Patent Number: 5,430,066
[45] Date of Patent: Jul. 4, 1995

[54] METHODS FOR PREVENTING WEIGHT LOSS, REDUCTION IN WEIGHT GAIN, AND ANOREXIA DUE TO IMMUNE STIMULATION

[75] Inventors: Mark E. Cook; Michael W. Pariza, both of Madison, Wis.

[73] Assignee: Wisconsin Alumni Research Foundation, Madison, Wis.

[21] Appl. No.: 875,896

[22] Filed: Apr. 29, 1992

[51] Int. Cl.$^6$ ............................................. A61K 31/20
[52] U.S. Cl. ..................................................... 514/558
[58] Field of Search ................................. 514/560, 558

[56] References Cited

U.S. PATENT DOCUMENTS

| 4,603,142 | 7/1986 | Burger et al. | 514/456 |
| 4,868,001 | 9/1989 | Maruta | 514/560 |
| 5,017,614 | 5/1991 | Pariza et al. | 514/558 |
| 5,070,104 | 12/1991 | Pariza et al. | 514/549 |

FOREIGN PATENT DOCUMENTS

| 294982 | 9/1986 | Japan | 514/560 |

OTHER PUBLICATIONS

*The Merck Index* 10th Ed. No. 5332, 1983.
*The Merck Veterinary Manual*, 5th Ed. pp. 1340–1343 and 1374–1379, 1980.
Y. L. Ha; N., K. Grimm and M. W. Pariza, in *Carcinogenesis*, vol. 8, No. 12, pp. 1881–1887 (1987).
Y. L. Ha; N., K. Grimm and M. W. Pariza, in *J. Agric. Food Chem.*, vol. 37, No. 1, pp. 75–81 (1987).
M. W. Pariza, Food Research Institute 1988 Annual Fall Meeting, Oct. 12, 1988.

*Primary Examiner*—Raymond Henley, III
*Assistant Examiner*—K. Weddington
*Attorney, Agent, or Firm*—Quarles & Brady

[57] ABSTRACT

Animal feed or human food which contains added conjugated linoleic acids (CLA) can enhance growth and prevent anorexia and weight loss due to immune stimulation (e.g., endotoxin exposure) and the adverse effects of catabolic hormones (i.e., IL-1). Methods of treatment using CLA also are disclosed.

7 Claims, No Drawings

METHODS FOR PREVENTING WEIGHT LOSS, REDUCTION IN WEIGHT GAIN, AND ANOREXIA DUE TO IMMUNE STIMULATION

This invention was made with United States Government support awarded by the United States Department of Agriculture (USDA), Hatch Funds. The United States Government has certain rights in this invention.

FIELD OF THE INVENTION

The present application generally relates to an animal feed additive and a pharmacologic agent for use in humans. More particularly, it relates to a feed additive/pharmacologic agent which prevents weight loss or reduction in the rate of weight gain and to methods relating to its use.

BACKGROUND OF THE INVENTION

Researchers have observed anorexia and weight loss or reduction in weight gain in humans and animals that have been exposed to immune stimulants, such as endotoxin (LPS). The intraperitoneal injection of lipopolysaccharide (i.e. endotoxin) into chickens decreases food intake and growth rate for 24 hours, alters nutrient metabolism, and induces fever.

Recent studies (Klasing et al., 1987, J Nutr. 117:1629) have confirmed that the vaccination of domestic fowl with several immune stimulants also can result in a substantial reduction in feed intake and induce weight loss or decreases in weight gain. In a study recently conducted with white Pekin ducks, two vaccinations reduced final carcass weight by as much as 0.4 lbs./bird and breast meat by 0.075 lbs./bird. Broilers and Single Comb White Leghorns (egg laying chickens) also have been observed to have reduced weight gains following immune stimulation. The potential losses due to immune stimulation costs the poultry industry millions of dollars per year. At the present time, antibiotics are used to prevent such weight loss but the use of antibiotics for this purpose is expensive and not without disadvantages.

In a similar manner anorexia, weight loss, and reduced growth of humans that are subjected to chronic immune stimulation because of infections, surgery, or exposure to immune stimulants is devastating to health and well being.

The mechanism by which immune stimulation causes anorexia, weight loss and reduced growth is known to be mediated by catabolic hormones released following immune stimulation (i.e., macrophage cytokine known as interleukin-1 or IL-1). The production of IL-1 from macrophages simultaneously stimulates T-cells to release IL-2, an anticarcinogenic compound which is desirable, but the release of IL-1 and other catabolic hormones from stimulated macrophages and possibly other immune-regulated cells induces an undesirable systemic reduction in skeletal muscle synthesis and increased muscle degradation resulting in weight loss or a decline in weight gain. Thus, while IL-1 and related immune hormones are essential cytokines for immune function, their systemic hormonal effects are devastating and have prevented its acceptance for immune therapy.

There is a need for feed additives, pharmacologic agents, and methods which can enhance growth and prevent the weight loss and anorexia that follows immune stimulation. There also is a need for a feed additive, pharmacologic agent, and method that can counteract the adverse effects of IL-1 and other hormones that induce tissue catabolism.

BRIEF SUMMARY OF THE INVENTION

It is an object of the present invention to disclose a feed additive, pharmacologic agent, and methods of using the feed additive and pharmacologic agent which prevent the weight loss and anorexia following immune stimulation.

It also is an object to disclose a method to counteract the adverse effects of catabolic hormones, such as IL-1.

We have discovered that the conjugated linoleic acids 9,11-octadecadienoic acid and 10,12-octadecadienoic acid (CLA) are valuable animal feed additives and potential pharmacologic agents which can enhance growth and prevent the weight loss that follows immune stimulation in animals, including humans. We also have discovered that the administration of safe and effective amounts of CLA to an animal can prevent the adverse effects of immune stimulation.

It will be apparent to those skilled in the art that the forementioned objects and other advantages may be achieved by the practice of the present invention.

DESCRIPTION OF THE PREFERRED EMBODIMENT

In a preferred embodiment of the invention a safe and effective amount of CLA is added to the food of an animal or human which has been or may be subjected to vaccination or other exposure to immune stimulants. The amount of CLA to be used as a feed or food additive is an amount which is safe and effective under conditions of use to prevent weight loss and/or enhance the growth of the animal to which it is administered. Because of the difference in size and susceptibility of animals and humans to the adverse effects of immune stimulation the amounts which are safe and effective will vary considerably. However, since CLA is a natural food ingredient and it is relatively non-toxic, the amount which can be administered is not critical as long as it is enough to be effective.

The practice of the present invention is further illustrated by the examples which follow:

EXAMPLE 1

Four pens of 10 chicks were fed a standard poultry ration with 0.5% lard (controls) or with 0.5% CLA mixed daily (2 pens per treatment). When the chicks were 3 weeks of age, they were weighed, inoculated with 100 μg of *E. Coli* 0111:B4 endotoxin i.p. to stimulate the immune system. Chicks were again weighed 24 h later. While the chicks feed the unsupplemented diet failed to gain body weight following endotoxin exposure, the chicks fed CLA gained 10 grams (p<0.07) (Table I). Antibody responses to sheep red blood cells demonstrated that CLA had no effect on antibody synthesis.

TABLE 1

| Treatment | Av. Initial Wt. | Av. Wt. 24h post endotoxin | Av. initial 24h | % with no or negative gain |
|---|---|---|---|---|
| Control | 311 ± 12 | 311 ± 12 | 0 ± 3 | 53 |
| .5% CLA | 305 ± 9 | 315 ± 9 | 10 ± 4 | 27 |

EXAMPLE 2

Another group of chicks were fed a diet containing 0.5% CLA which was mixed with the feed daily. At 3 weeks of age the chicks were inoculated i.p. with 750 μg $E.$ $Coli$ 055:B5 endotoxin to stimulate immunity or phosphate buffered saline (PBS) as a control. The control chicks injected with PBS gained 9 g over the following 24 h period, and the CLA fed, PBS injected chicks gained 13.5 g. When chicks fed the control diet were injected with endotoxin, they lost 1.3 g of body weight over the following 24 h period. However, the CLA fed chicks even after endotoxin injection continued to gain an average of 6.6 g.

The results of the examples demonstrate that a lower proportion of chicks lose weight, within 24 hours of being injected with endotoxin, when the chicks ingest an animal feed which contains CLA. In fact, the results show that not only do a fewer number of birds lose weight but that those birds that are fed CLA actually gain considerably more weight than the control birds. In addition, the loss of body weight in rats following stimulation was 50% of those not fed CLA.

In addition to using CLA as an animal feed additive (e.g. poultry feed) to enhance growth and prevent weight loss by diminishing the effects of immune stimulation, CLA is useful as an immune modulator (e.g. IL-1 inhibitor). The adverse or harmful catabolic effects of systemic IL-1 may be alleviated by adding CLA to the food of animals, including humans, experiencing weight loss associated with acute or chronic diseases.

EXAMPLE 3

A group of seven rats was fed a semi-purified diet to which CLA was not added; a second group was fed the same diet containing 0.5% CLA. Three weeks later the animals were weighed. Four animals from each group were inoculated with endotoxin (1 mg/kg body weight); the remaining three animals from each group were inoculated with PBS. Rats fed the control diet and injected with PBS gained 7.4 g. Rats fed the CLA-containing diet and injected with PBS gained 5.4 g. Rats fed control diet and injected with endotoxin lost 21.05 g. Rats fed CLA-containing diet and injected with endotoxin lost only 11.9 g.

In another embodiment of the invention a fatty acid that is converted into CLA or which modulates the level of CLA in the body of an animal or a human is fed. Specifically, we have found that linoleic acid is converted to CLA in the bodies of rats, probably by microorganisms in the gastrointestinal system (S. F. Chin, W. Liu, K. Albright, and M. W. Pariza, 1992, FASEB J. 6:Abstract #2665).

EXAMPLE 4

A group of seven rats was fed a semi-purified diet containing 5% corn oil; a second group was fed the same diet with corn oil but also containing added free linoleic acid (0.5%). Three weeks later the animals were weighed. Four animals from each group were inoculated with endotoxin (1 mg/kg body weight); the remaining three animals from each group were inoculated with PBS. Rats fed the control diet and injected with PBS gained 7.4 g. Rats fed the diet to which linoleic acid had been added, and injected with PBS, gained 7.2 g. Rats fed control diet and injected with endotoxin lost 21.05 g. Rats fed diet to which linoleic acid had been added, and injected with endotoxin, lost only 11.4 g. We believe these results are due to the conversion of added linoleic acid to CLA within the body of rats as discussed above.

The methods of the present invention may take several embodiments. In one embodiment, the CLA is added to an animal's feed or to a human's food. In another embodiment, the CLA can be administered to an animal in a pharmaceutical or veterinary composition containing a safe and effective dose of the CLA. In a third embodiment, the animal can be fed a safe amount of the reactants which will form the CLA in situ in the animal or human.

The novel animal feeds and pharmaceutical preparations of the present invention are those containing the free conjugated linoleic acids (CLA) 9,11-octadecadienoic acid and 10,12-octadecadienoic acid in combination with a conventional animal feed (e.g. poultry feed), human food supplement, or approved pharmaceutical diluent. Active forms of CLA also include compositions containing the active isomers of CLA; non-toxic salts thereof; active esters and other active chemical derivatives thereof; and mixtures thereof. Animals and humans may also be given a substance such as linoleic acid which is converted to CLA within the body, or which may modulate intracellular levels of CLA or otherwise mimic the beneficial effects of CLA in mitigating anorexia, weight loss, and reduced growth resulting from immune stimulation.

The free conjugated linoleic acids (CLA) have been previously isolated from fried meats and described as anticarcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). However, animal feeds containing CLA, or its non-toxic derivatives, such as the sodium and potassium salts, as an additive in combination with conventional animal feeds or human foods are novel.

The free acid forms of the CLA may be prepared by isomerizing linoleic acid. The non-toxic salts of the free CLA acids may be made by reacting the free acids with a non-toxic base. Natural CLA may also be prepared from linoleic acid by the action of $\Delta^{12}$-cis, $\Delta^{11}$-transisomerase from a harmless microorganism such as the Rumen bacterium $Butyrivibrio$ $fibrisolvens.$ Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

To enhance growth, prevent weight loss or counteract the adverse effects of catabolic hormones, the CLA and its non-toxic derivatives, such as the non-toxic salts, in addition to being added to an animal's feed or human food or formed in situ can be administered in the form of pharmaceutical or veterinary compositions, such as tablets, capsules, solutions or emulsions to the animal or the humans. The exact amount to be administered, of course, depends upon the form of CLA employed, the route of administration, and the nature of the animal's or human's condition or disease. Generally, the amount employed of CLA and its non-toxic salts employed as a pharmaceutical will range from about one part per million (ppm) to about 10,000 ppm of CLA in the animal's or human's diet. However, the upper limit of the amount to be employed is not critical because CLA is relatively non-toxic and it is a normal constituent of the human diet (including human breast milk). The amounts to be added to a conventional animal feed or human's food as an additive can range from 0.01% to 2.0% or more by weight of the animal's or human's food.

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

It will be readily apparent to those skilled in the art that a number of modifications or changes may be made without departing from the spirit and scope of the present invention. Therefore, the invention is only to be limited by the claims.

We claim:

1. A method of preventing weight loss, reduction in weight gain or anorexia in an animal caused by immune stimulation of the animal by endotoxin, said method comprising administering orally or parenterally to said animal a safe amount of a member selected from a conjugated linoleic acid, free linoleic acid, salts thereof and mixtures thereof, said amount being effective to prevent the weight loss, reduction in weight gain or anorexia caused by the immune stimulation.

2. A method of claim 1 in which the animal is a bird.

3. A method of claim 1 in which the conjugated linoleic acid is selected from 9,11-octadecadienoic acid and 10,12-octadecadienoic acid.

4. A method of alleviating the adverse catabolic effects produced by a product of the immune system which is released after immune stimulation of an animal by endotoxin, said method comprising orally or parenterally administering to said animal a safe amount of a member selected from a conjugated linoleic acid, free linoleic acid, salts thereof and mixtures thereof, said amount being effective to alleviate said adverse catabolic effects produced by a product of the immune system.

5. A method of claim 4 in which the conjugated linoleic acid is selected from 9,11-octadecadienoic acid and 10,12-octadecadienoic acid.

6. A method of alleviating the adverse catabolic effects produced by interleukin-1, said method comprising administering orally or parenterally to an animal a safe amount of a member selected from a conjugated linoleic acid, free linoleic acid, salts thereof and mixtures thereof, said amount being effective to alleviate said adverse catabolic effects.

7. A method for improving an animal food so as to prevent the weight loss, the reduction in weight gain or the anorexia which can be caused by immune stimulation of an animal by endotoxin, said method comprising adding to an animal food a member selected from 9,11-octadecadienoic acid; 10, 12-octadecadienoic acid; and mixtures thereof, so that the food contains about 0.1% to about 2.0% by weight of the food, said amount being effective when the food is fed to an animal to prevent the weight loss, the reduction in weight gain or the anorexia caused by immune stimulation.

* * * * *